(12) United States Patent
Truex et al.

(10) Patent No.: US 8,480,957 B2
(45) Date of Patent: Jul. 9, 2013

(54) SYSTEM FOR VISUAL AND ELECTRONIC READING OF COLORIMETRIC TUBES

(75) Inventors: Bryan I. Truex, Belleair Beach, FL (US); Gueorgui Mihaylov, Virginia Beach, VA (US)

(73) Assignee: Nextteq LLC, Tampa, FL (US)

( * ) Notice: Subject to any disclaimer, the term of this patent is extended or adjusted under 35 U.S.C. 154(b) by 0 days.

(21) Appl. No.: 13/227,177

(22) Filed: Sep. 7, 2011

(65) Prior Publication Data
US 2012/0063956 A1 Mar. 15, 2012

Related U.S. Application Data

(60) Provisional application No. 61/380,582, filed on Sep. 7, 2010.

(51) Int. Cl.
*G01N 30/96* (2006.01)
*G01J 1/48* (2006.01)
*G01N 31/00* (2006.01)
*G01B 11/14* (2006.01)

(52) U.S. Cl.
USPC ............. 422/69; 702/24; 422/63; 422/86; 422/88; 356/617

(58) Field of Classification Search
USPC ............. 356/167, 201; 422/69, 917; 702/24
See application file for complete search history.

(56) References Cited

U.S. PATENT DOCUMENTS

| | | | | |
|---|---|---|---|---|
| 4,063,821 | A * | 12/1977 | King et al. | 356/634 |
| 6,547,910 | B1 * | 4/2003 | Benzing et al. | 156/212 |
| 7,355,697 | B2 * | 4/2008 | Mertz et al. | 356/246 |
| 7,465,427 | B2 * | 12/2008 | Truex et al. | 422/82.05 |
| 2008/0176317 | A1 * | 7/2008 | Kirollos et al. | 435/288.7 |
| 2008/0186494 | A1 * | 8/2008 | Kiesel et al. | 356/440 |

* cited by examiner

*Primary Examiner* — Jill Warden
*Assistant Examiner* — Julie Tavares
(74) *Attorney, Agent, or Firm* — Bernard G. Pike; Pike IP Law, PLLC

(57) ABSTRACT

Gas detector tubes may be used to determine a concentration of target gases in air. The gas detector tubes described may be read either by and optical reader or visually by the user. A gas detector tube reader having an optical reader capable of reading a length of stain, a color change and color density of a reagent in a gas detector tube. The gas detector tube may further comprise sensors for measuring the environmental conditions during sampling.

17 Claims, 8 Drawing Sheets

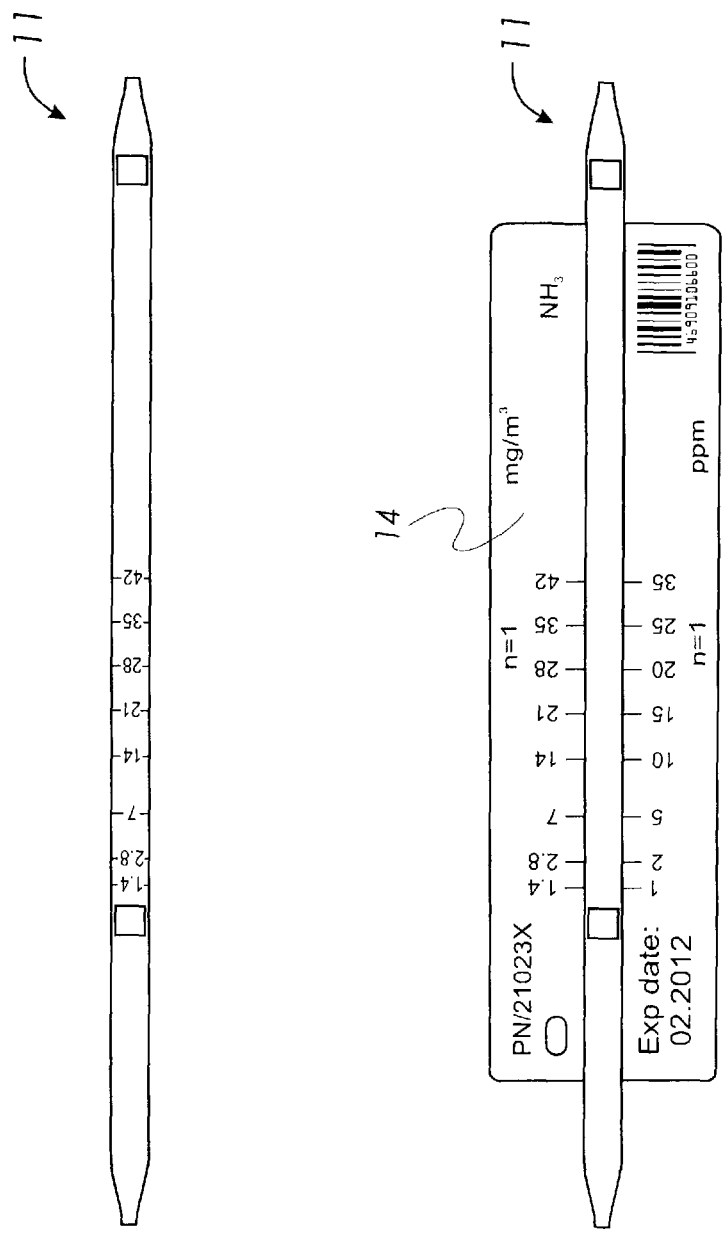
FIG.2-A

SYSTEM FOR VISUAL AND ELECTRONIC READING OF COLORIMETRIC TUBES

RELATED PATENT APPLICATIONS

This patent application claims priority under 35 U.S.C. §119 to U.S. Provisional Patent Application No. 61/380,582 filed on Sep. 7, 2010 which is hereby incorporated by reference in its entirety.

FIELD OF THE INVENTION

The invention relates to gas detector tubes and an apparatus for sampling. Embodiments of the apparatus are capable of detecting and determining an approximate concentration of at least one component of a gas mixture. Embodiments of the apparatus comprise a system for colorimetric detection of certain components of a gas by color change of a chemical reagent. The resulting color change may be optically measured as a length-of-stain that is proportional to the reacted quantity of the target gas or as a level of color difference between unchanged and changed by chemical reaction color. In embodiments of the gas detector tube, the length of stain and/or color change may be determined visually or electro-optically.

BACKGROUND OF THE INVENTION

There are a variety of apparatuses for measuring the concentration of certain gaseous components of a gas mixture. One simple apparatuses, referred to as gas detector tubes or gas indication tubes, typically comprise a glass or other transparent tube and a chemical reagent that is capable of reacting with a target chemical compound resulting in a color change of the reagent.

Conventional gas detector tubes are glass tube filled with a chemical reagent that reacts to a specific chemical or family of chemicals. The chemical reagent is sealed within the glass tube and retained in position by gas permeable plugs on either end of the glass tube. In some cases, the chemical reagent may be liquid impregnated into a porous chemically neutral solid substrate. The chemical reagent is protected from exposure to contaminants and chemical compounds by sealing the tubes at each end until use and, therefore, extending the shelf life. To use the gas detector tube, the tips are broken to open a flow path through the tube and across the reagent. The air to be sampled may then be drawn through the tube and in contact with the reagent using a fixed volume sampling pump, for example. The reagent layer is capable of rapidly reacting with the target chemical compounds as the air to be sampled is drawn through the tube. The amount of reaction and the change of color of the reagent are related to the concentration of the target chemical compounds in the sampled gas and the volume of gas drawn through across the reagent.

To determine the gas concentration, a known volume of gas may be drawn into the tube and the concentration of the gas is the only variable. The length of the color change or the degree of color change of the reagent then corresponds to the concentration of the target compounds. Detector tubes that measure gas concentration by length of stain or length of color change are reliable and simple to use. Currently, detector tubes relying on measurement of the intensity or density of the generated color are not used because of difficulties in creating an appropriate set of color standards to indicate the concentration of the gas.

After manufacturing a batch of length of stain detector tubes, known concentrations of target gases are passed through the gas detector tubes to develop a batch specific a calibration curve relating the length of stain to a corresponding gas concentration. The calibration curve is included with the detector tube to allow visual reading of the concentration of a gas in a sampled volume. From their first introduction the detector tubes have their scale printed separately, see, for example, U.S. Pat. No. 2,174,349 to J. B. Littlefield. As the leading edge of color change of the reagent in the detector tubes is not always well defined, the scale divisions may be marked having a distance greater than length of diffusive front of discoloration. As such, the scales are of poor resolution and, more recently, the scales printed directly on the surface of the tube. For example, Dreager™, Gastec™, Kitagava™, Auer™, MSA™, RAY™, as well as other manufacturers of detector tubes have on their tubes the beginning of the scale—first scale division, marked 3 to 5 mm from the end the first input plug. Because of possible channeling effects, resulting in different lengths visible on each side of the tube, the divisions are printed as rings around the tube and numbers representing concentrations are in close proximity or into broken portion of the ring. The drawback of the known art is that such detector tubes cannot be read by electronic device because of the concentration lines, concentration amounts, and other marks on the tubes obstructing optical reading of the length of stain. For example, the markings may be interpreted by the device as a color change.

There has been a long felt need for a better more accurate and objective way of reading gas concentration with gas detector tubes. Heim et al. in U.S. Pat. No. 4,123,227 show a length-of-stain tube electronic reader based on detector tube without any printed matter. The detector tube serves as an alarming device and is periodically interrogated over a period of time. Leichnitz et al. in U.S. Pat. No. 5,069,879 suggested a tube having no scale on the readable part of the surface and printed means introducing into electronic reader all specific data for the tube including calibration data. There is a significant drawback of the tubes manufactured to be read by electronic reader only; they may not also by read visually.

The contemporary art of colorimetric reading devices is developed in the direction of devices even more specifically designed for optic-electronic reader. U.S. Pat. No. 5,089,232 to May shows an arrangement of tube-like devices for only electronic reading. U.S. Pat. No. 5,397,538 to Stark et al., U.S. Pat. No. 5,415,838 to Rieger et al. and U.S. Pat. No. 5,464,588 to Bather at al. depict development of specific tube-like devices for electronic reading of a zone of discoloration. Such devices however are highly specific and cannot be read without specialized electronic means.

All color change indicated by colorimetric reactions of the reagent depend to some extend on the ambient conditions—temperature, relative humidity and barometric pressure.

Temperature and relative humidity correction factors are typically provided by the manufacturer for a specific reagent and target compound. Like calibration curves the correction factors may be calculated on a batch basis. The correction factors should be applied to the concentration indicated by the length of stain in the detector tube and to more accurately determine the actual target gas concentration. The atmospheric pressure has two components altitude above sea level and weather factors. The altitude component is generally a larger factor in determination of the atmospheric pressure than the weather factors (usually much less than 1%). Weather factors may be considered negligible. The altitude of the gas detector above sea level, however, may have a significant outcome on determination of the actual concentration. In some cases, the measured concentration may be considerably below of the actual concentration.

TABLE 1

Atmospheric Pressure Function of Altitude

| Altitude (km) | Pressure (mb) | Correction |
|---|---|---|
| 0.0 | 1013.25 | 100.0% |
| 0.5 | 954.61 | 94.2% |
| 1.0 | 898.76 | 88.7% |
| 1.5 | 845.59 | 83.4% |
| 2.0 | 795.01 | 78.4% |
| 2.5 | 746.91 | 73.7% |
| 3.0 | 701.21 | 69.2% |
| 3.5 | 657.80 | 64.9% |
| 4.0 | 616.60 | 60.8% |
| 4.5 | 577.52 | 56.9% |
| 5.0 | 540.48 | 53.3% |
| 5.5 | 505.39 | 49.8% |

Typical detector tubes also show an increasing sensitivity to color change with an increase in temperature. Therefore, gas detector tubes may also require compensation for temperature. The following table, Table 2, shows the temperature compensation factors for a Gastec™ gas detector tube for determination of the concentration of 1, 1 trichloroethylene in air:

TABLE 2

| Temperature, °C. | 0.0 | 10 | 20 | 30 | 40 |
|---|---|---|---|---|---|
| Correction factor | 1.4 | 1.3 | 1.0 | 0.8 | 0.65 |

The following table, Table 3, shows the compensation factors for a particular gas detector tube manufactured by Gastec for determination of the concentration of hydrazine in air:

TABLE 3

| Relative Humidity % | 10 | 30 | 50 | 70 | 90 |
|---|---|---|---|---|---|
| Correction factor | 0.8 | 0.9 | 1.0 | 1.2 | 1.4 |

Determination of a more accurate estimation of an actual concentration using gas detector tube should incorporate one or more of these compensation factors for environmental conditions. There is a need for a measurement system that provides automatic compensation of these parameters.

SUMMARY

Embodiments of the gas detector tubes may be read either visually or by an electronic gas detector tube reader with any obstruction of the reagent. Further, embodiments include gas detector tubes comprising a gas detector tube surface that does not comprise marking or shading that obstruct view of at least a portion of the reagent. The detectors may comprise 2 to 4 different scales for visual reading of the gas concentration on extensions or scale wings of the gas detector tubes. The extensions or scale wings provide a sufficient surface area for a variety of visually and optically or electronically readable information. The scales may be for 1-5 strokes, or more, an appropriate gas detector pump and/or in two formats such as, but not limited to, $mg/m^3$ and ppm. In addition to the scales, the gas detection tubes may further comprise optical information for the calibration of a data readable optic-electronic gas detector tube reader. In an embodiment, the gas detector tube comprises a sealed transparent tube, a chemical reagent capable of a colorimetric reaction with a gaseous chemical compound within the sealed transparent tube, at least one elongated extension or wing scale extending from the tube; and at least one length of stain measurement scale on the extension. The gas detector tube may further comprise a transparent plastic adhered to a surface of the transparent tube and a surface of the elongated extension. Embodiments also include an optic-electronic gas detector tube reader capable of reading such detector tubes such as by comprising an optical reader. As used herein, an "optic-electronic reader" or an "optical reader" is a computer device that captures visual information and translates the image into digital information the computer is capable of understanding and displaying. The visual information may be two or three dimensional information and include the color and shape of visual information. The "optic-electronic reader" or an "optical reader" may include illuminating device and a light sensor for interpreting the light reflected from an object. As used herein, "visual" means as interpreted by the human eye and brain.

Embodiments of a gas detector tube reader may comprise a holder for receiving a gas detector tube, an information reader capable of reading electronic or optically coded information from the gas detector tube, an optical reader system capable of determining the length of stain in the gas detector tube, and a central processing unit to estimate the target gas concentration from the outputs of the sensors. Embodiments of the optic-electronic gas detector tube reader are capable of compensating for any effects on reading as a result of relative humidity, temperature and altitude.

The optic-electronic gas detector tube reader can read the various calibration data from each gas detector tube. The calibration data, measured data and compensated data may then be output and displayed on a display of the optic-electronic gas detector tube reader and/or communicated to another processing unit for display and recordation. The data may include, but is not limited to, the type of tube, target gases, measuring range of the tube, tube accepted/rejected upon introduction of an internal standard and/or expiration date, concentration measured, environmental conditions including, but not limited to, relative humidity, temperature, barometric pressure, as well as total % of compensation applied to the measured gas concentration.

Embodiments of the method of determining a concentration of a gaseous compound, comprising placing a tube in an optic-electronic gas detector tube reader, electronically reading information from the gas detector tube, and displaying an acceptance or rejection of the tube based upon the expiration date of the tube and/or any prior discoloration of the reagent. The method may further comprise drawing a known volume of gas sample through the gas detector tube and optically reading the length of stain. After sampling, if applicable, the readout of the optic-electronic gas detector tube reader may display information including, but not limited to, a measured gas concentration, the compensation factors to be applied to the measured gas concentration, each compensation factor determined from a measurement of the ambient conditions sensors including, but not limited to, temperature, relative humidity and barometric pressure or altitude, for example.

Embodiments of the gas detector tubes and gas detector tube readers allow use of the gas detection by gas detector tubes both visually and optic-electronically and allow a more accurate and flexible way of utilizing the gas detector tubes.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

BRIEF DESCRIPTION OF THE DRAWINGS

The invention will now be described with the reference to the drawings wherein:

FIG. 1-C is a cross-section of the tube assembly with one scale wing; FIG. 1-D is a gas detector tube with prismatic cross-section with scales along the walls or along the edges of prism; FIG. 1-E is a gas detector tube with a hexagon cross-section with scales along the walls; FIG. 1-F is a cross-section of gas detector tubes attached on the holder for transportation and storage; and FIG. 1-G is a gas detector tube with square cross-section with scales along the walls;

FIG. 2A depicts a side-by-side comparison between a prior art gas detector tube (top) and an embodiment of a gas detector tube comprising extensions.

FIG. 3-A is a perspective view of the two shells (jaws) of the reading head of a gas detector tube reader;

FIG. 3-B is a cross-section of the jaws over a gas detector tube with marked direction of light;

FIG. 5-A Front of tube with scale wings and FIG. 5-B is a side view of scale wings in locked position;

FIG. 7-A shows the process cycle in a fixed range and predetermined fixed sampling volume, B and B1 are points of color saturation followed by immediate integration at very high concentration before end of stroke—point A and FIG. 7-B is a process cycle in very low concentration mode urging user to perform more strokes until first color change is detected—points C and C1 and FIG. 7-C is a graph showing a vacuum pressure check mode.

DESCRIPTION OF PREFERRED EMBODIMENTS OF THE INVENTION

Figure 1:
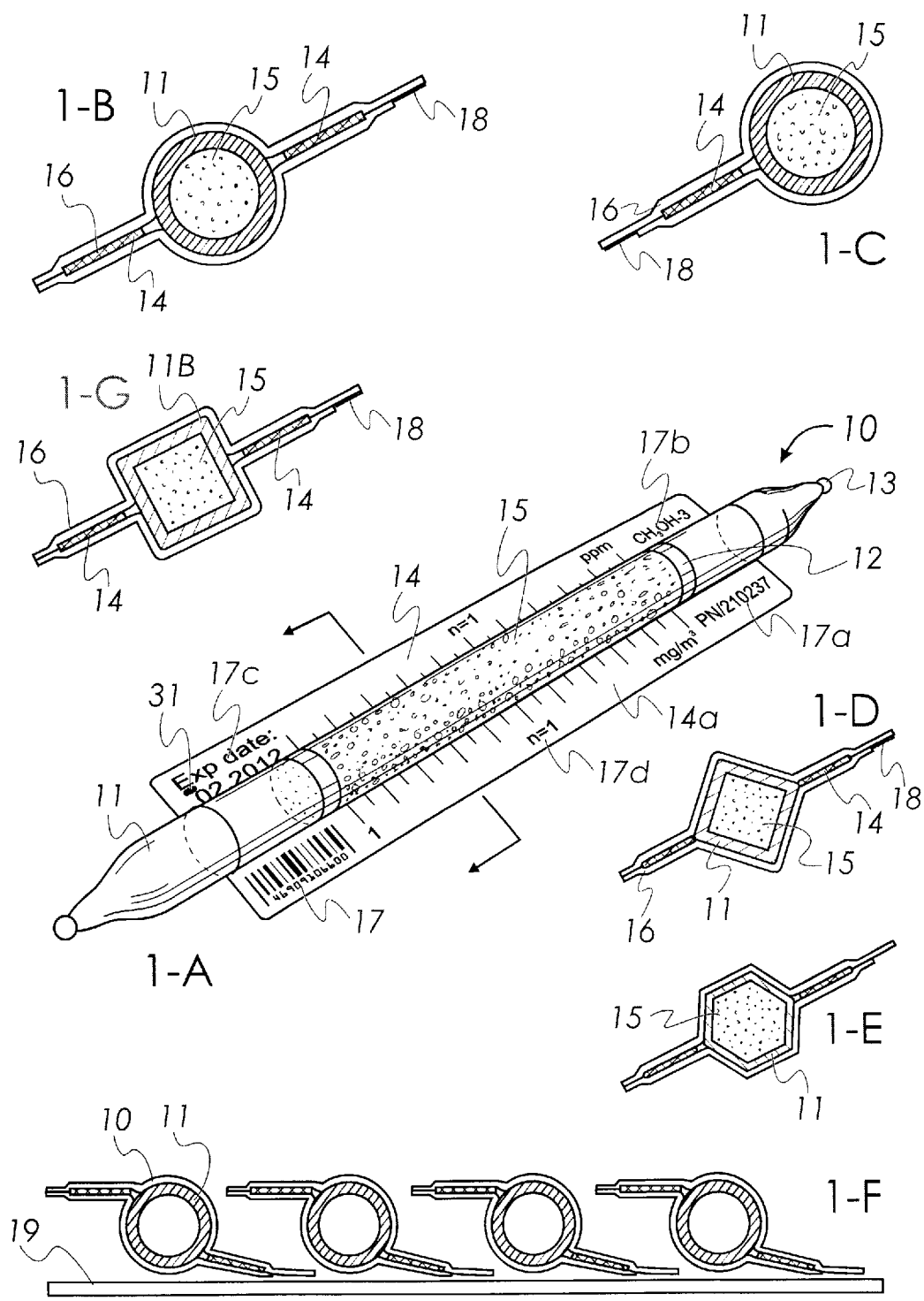
FIGS. 1-A to 1-G depicts colorimetric gas detector tubes comprising at least one extension or scale wing; wherein FIG. 1-A is a perspective view of the tube assembly with planar extensions, FIG. 1-B is a cross-section of the tube assembly with two scale wings.
Figure 2:
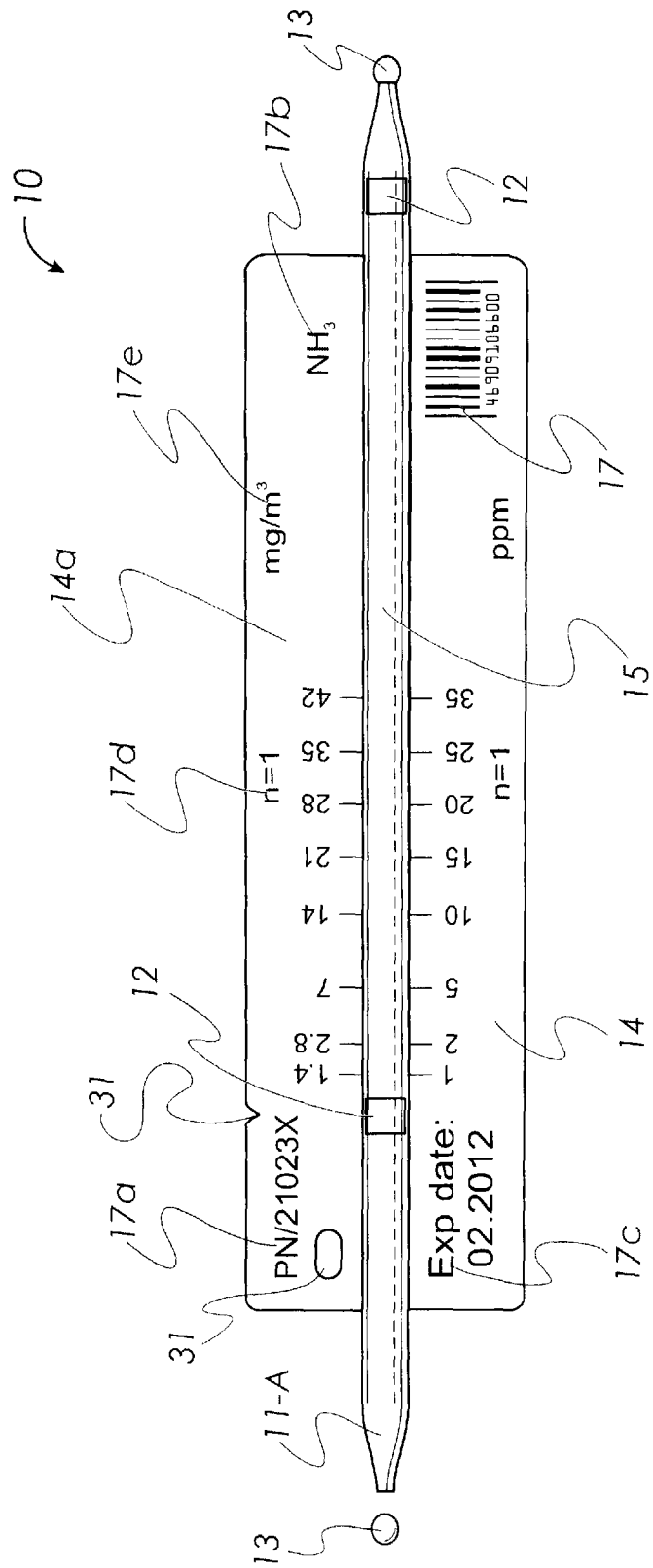
FIG. 2 depicts a front view of colorimetric gas detector tube assembly with sidewise scales.

Gas detector tubes may be used to determine the concentration of at least one target gas, family of target gases comprising a similar functional group, or class of target gases (collectively "target gases") in a sample gas. The gas detector tubes typically comprise a chemical reagent within a transparent tube. Gas detector tube may comprise one or more chemical reagents that indicate the presence of specific target gases. Typical chemical reagents for gas detector tubes comprise a porous solid with pathways that allow gas to flow through the porous solid from an inlet of the gas detector tube to an outlet of the gas detector tube or the chemical reagent is on the surface of a porous solid substrate. The chemical reagent will change color when the reagent is in contact with the chemical reagent ("colorimetric reaction"), typically the chemical reagent and the target gases will react resulting in the color change. As a sample passes through the gas detector tube, the target gases are involved in the colorimetric reaction with the chemical reagent until the target gases are depleted from the sampled gas. Many reagents for use in gas detector tubes are known and applicable to embodiments of the gas detector tubes. A sample is typically drawn through the gas detector tubes by a sampling pump. Common sample pumps include hand-held piston pumps or bellows pump that are capable of accurately and repeatedly drawing a known volume of air.

Typically, the chemical reagent is fixed in place within the tube by two porous solid plugs at either end of the reagent. As the gas comprising target gases is drawn through an inlet of the gas detector tube, the chemical reagent near the inlet will begin to change color and, if the concentration of the target gases is with the readable range of the gas detector tube, the chemical reagent near the exit of the tube will remain unchanged. The length of the color change of the reagent ("length of stain") within the tube will correspond to the total amount of the target gases that were passed through the gas detector tube. In a known volume of gas is passed through the tube, a concentration of the target gases may be determined. Conventional gas detector tubes have a scale printed on the glass tube over the chemical reagent that may be used to approximate the concentration of the target gases for a known volume of the sampled gas. Each gas detector tube will have a readable concentration range of target gases, if the gas concentration range is exceeded for a volume of sample, the chemical reagent will change color throughout its entire length and a concentration of the target gas may not be conventionally determined or if the concentration of the target gas is too low, the chemical reagent may not record a sufficient color change to determine the concentration of target gases. In such cases, a different tube with the appropriate concentration range may be used or the volume of sampled gas may be increased or decreased to produce a reading within the scale. For some gas detector pump and gas detector tube systems, up to a five-fold increase in sampled volume is recommended. The scale of the gas detector tube must then be adjusted to account for the different sample volume.

Embodiments of the gas detector tubes of the invention may be read either electronically by an electronic gas detector tube reader or visually by a user by a simple comparison of the length of stain with one or more scales on an extension of the transparent body. Specific embodiments of the gas detector tubes comprise a sealed transparent tube; a chemical reagent capable of a colorimetric reaction with a target gas within the sealed transparent body and at least one elongated extension extending from the body comprising both electronically readable indicia and visually readable indicia. Unlike conventional gas detector tubes, the indicia are not on the transparent body and, therefore, will not interfere with electronic reading of the length of stain. Embodiments include gas detector tubes comprising a transparent tube or transparent body surface that do not comprise marking or shading that obstruct view of at least a portion of the reagent for optic-electronic reading of the length of stain.

Embodiments of the gas detector tubes may further comprise a transparent plastic covering adhered to the surface of the body. The extensions may be formed from the transparent plastic covering or the extensions may also be covered by the transparent plastic covering.

Gas Detector Tubes

The gas detector tubes may comprise a transparent tube. During storage and prior to use the transparent tube may be a sealed tube. As used herein, "tube" means a conduit defining a flow path of any cross-sectional shape. The cross-sectional shape may be circular, oval, rectangular, square, rectangular, polygonal or any desired cross-sectional shape. As used herein, "sealed tube" means the tube is closed such that it creates an inner volume within the sealed tube that is not substantially exposed to an environment external to the tube. The tube may be sealed simply by heating and pinching the ends of the tubes to seal the tube, using caps, septums or other means to seal the tube. Embodiments of the gas detector tubes may comprise a transparent tube made from a glass or transparent plastics such as but not limited to, acrylic, polycarbonates, copolymers of polyethylene and polypropylene, polyesters as well as other transparent materials.

In further embodiments, the gas detector tube may comprise a transparent tube and a transparent plastic adhered to a surface of the transparent tube. For example, the outer surface of the transparent tube may be wrapped by thin optically clear conformable plastic adhered by a neutral transparent adhesive layer. The gas detector tubes may have one or more extensions or "scale wings". In some embodiments wherein the indicia are to be optically read by the gas detector tube reader, the extension may comprise or form pockets for the printed scales, the pockets comprise a transparent window allowing illumination and reading of the coded information.

Extensions

The gas detector tubes may further comprise one or more extensions or scale wings. The extensions extend outwardly from the surface of the transparent tube and form a surface for printing, etching, embossing, attaching, encapsulating, holding, or otherwise providing a scale for reading the length of stain resulting from sampling with the gas detector tube. The extensions or scale wings may extend substantially perpendicular from the transparent tube surface or a tangent to the transparent tube surface. As used herein, "substantially perpendicular" means within ten degrees of a ninety degree angle. As the scale is printed on the extensions, the transparent tube may not comprise any markings or shadings to obstruct electronic reading of the color change or length of stain of a reagent in a sampled tube. The extensions will typically be at least as long as a usable length of the reagent within the tube. In certain embodiments, the gas detector tubes comprise an extension that is an elongated rectangular shape attached to the transparent tube and extends along a length of the tube at least as long as a distance between the two porous plugs. In embodiments of the gas detector tubes that are capable of being read both visually and by an electronic gas detector tube reader, the indicia on the extension or scale wings will comprise both visually readable scale and electronically readable information is printed on the scale. In embodiments of the gas detector tubes comprising more than one extension and scale indicator, any of the extensions may comprise both visually readable scale and electronically readable information or only one of the visually readable scale and electronically readable information.

In certain embodiments, the gas detector tube may comprise a pocket for receiving a scale indicator comprising the indicia. The pocket may protect the scale indicator from exposure to the environment. After insertion of the scale indicator, the pocket may be sealed such as by an adhesive.

In additional embodiments, the gas detector tubes may comprise two extensions. The second extension may provide additional surface area or a second pocket for indicia to be provided on the gas detector tube. The additional indicia may include scales with different units of measure, scales for different volumes of sampled gas, a bar code, or other electronically readable information, for example. The extensions may be the same or different shape, the same or different size, in the same plane, in different planes or in substantially parallel planes. In embodiments of the gas detector tubes, the extensions and the transparent tube may be formed as a unitary part or as individual parts attached together. The transparent tube and extensions may be attached together by a transparent covering adhered to both the transparent tube and the extension or by an adhesive, or melting the parts together, for example.

As discussed, embodiments of the gas detector tubes are capable of being read both visually and by an electronic gas detector tube reader, the extensions may comprise a locating system for accurately placing the gas detector tube in the electronic gas detector tube reader. The locating system may be any components that are capable of aligning the gas detector tube in the reader. For example, the locating system may comprise a stops and/or a recess capable of receiving and securing at least one of the extension or the transparent tube or may simply comprise a pin and recess. One of the pin and recess may be located on the gas detector tube and the other of the pin and recess is located on the electronic gas detector tube reader. For example, one of the scale wings may comprise an oval recess which may be aligned with a pin in a reading head of a gas detector tube reader to thereby provide accurate and repeatable position of the tubes for reading.

Transparent Covering

Embodiments of the gas detector tube may further comprise a transparent covering. The covering may encapsulate at least a portion of the transparent tube and/or the extensions. The transparent covering may be a plastic that is conformable to at least a portion of an exterior of the tube and/or the extensions. The transparent plastic is adhered to the body by at least one of physical means, shrink wrapping, or adhesive. The adhesive may be a permanent neutral transparent adhesive layer. However, the transparent plastic should not interfere with reading of the length of stain of the reagent for either visual or electronic reading of the gas concentration.

The transparent covering may form pockets or otherwise encapsulate and/or secure the extensions to the transparent tube. The pockets may be fixed along the main axis of the tube so any scales on the extension may be retained in position adjacent to the chemical reagent. The scales may be single or double sided with scale marking on both sides to increase readability and flexibility in providing information and data.

In some embodiments, the transparent covering or the transparent tube may be colored similarly to the color of the unreacted chemical reagent or complementary to a color expected after the colorimetric reaction of the chemical reagent. Thus, the color of the transparent covering may be used to thereby filter the illuminating and reflected light of an optically readable gas detector tube reader to enhance the color contrast between reacted and unreacted reagent layer and increase the accuracy of the optical reader. The enhanced contrast may more clearly define the reacted portions of the reagent and the end of the length of stain in the tube may be more easily identified. The design allows additional filtration color or complemented color to be superimposed on the color changing reagent layer thereby increasing visual and optically read color contrast between pristine and reacted reagent.

The transparent covering may also comprise a tacky surface for more securely holding the gas detector tubes in a box for storage or transportation.

Printed Scales

The gas detector tubes comprise indicia and/or scales. The indicia may preferably be on the extensions or scale wings to leave an unobstructed view of the reagent. The visually readable indicia may be used at least to measure the length of stain produce by the gas detector tube after passing a sample through the tube. The length of stain corresponds to an uncompensated concentration of the target gas in the sample. The indicia and/or scales may be incorporated on the extension by any means including being printed, embossed, or etched directly on the extension, applied to the extensions with a label or card, and/or inserted within a pocket of the extension, for example. The scales are made from opaque preferably white material and positioned parallel to the main axis of the gas detector tube. The divisions of each scale may be printed, embossed or etched by any feasible art including laser printers and inkjet printers. As such, any batch to batch manufacturing differences in the production of the gas detector tubes may be encoded and printed along with other standard information pertaining to particular type of tube. For embodiments of the gas detector tubes to be electronically or optically read by a optic-electronic gas detector tube reader, the electronically or optically readable information may be included on the extensions. The optically readable indicia may be read by the optical reader, converted to digital information and understood by the central processing unit.

In embodiments of the gas detector tubes for both visual and electronic or optically reading of the tubes, the indicia for each use should not interfere with each other. For example, one set of information may be on the front and the other on the back or in different area on the same side, for example. The electronic or optically coded information may include the type of tube, exposure range, calibration curve, expiration date, pristine or unreacted color of the reagent, and allowable range of color change after certain edging, expected color change and density/saturation of the reacted and unchanged reagent material necessary for automated optic-electronic reading.

In addition to the electronically or optically readable information, the printed scales comprise visually readable information. The visually readable information may include, but is not limited to, type of tube, range of exposure, recommended strokes of sampling, expiration date, part and lot numbers. The scales may further include an indication such as an arrow, for example, indicating the direction of introducing the tube into reader and/or sampling air through it. In some embodiments, the electronically or optically readable information may be in a relatively small area and/or located in an area different than the visually readable information. The electronically readable information may be optically readable, electronically readable and/or wirelessly readable such as by radio frequency identification (RFID), for example.

In some embodiments, the printed scale may be adhered to or within a pocket of the extensions by the same adhesive that is used to adhere the transparent covering to the tube. Thus, the scales may be securely positioned in the appropriate location relative to the reagent to effectively allow determine a concentration of a gas in a sample from a color change in the colorimetric reagent. During the manufacturing process the beginning of each zero mark of the scale may be precisely aligned with the line separating reagent layer from the end of the reagent retaining plug adjacent to the inlet of the tube.

The indicia may include scales for different sampled volumes. For example, if a significant colorimetric reaction does not occur from a first volume of the gas to be sampled, such as a single stroke of a piston sampling pump, additional volume of the gas to be sampled may be drawn through the gas detector tube. The colorimetric reaction may not be significant relative to a specific gas detector tube in a color change does not occur or the color change does not extend into the readable concentration scale. In such case, additional volume of gas may be drawn through the gas detector tube, four more strokes of the piston 43 attached to piston shaft 45 may be used to observe color change, for example. If a color change still doesn't appear another 5 strokes may be necessary, however, not all types of gas detector tubes allow linear approximation of gas concentrations to that extent.

For the appropriate types of tubes, the indicia may include four scales marks appropriate for required volume of air necessary to produce a readable length of stain in the reagent. The additional scales may be on the both sides of the extensions. The indicia may also include scale for determination of the gas concentration in different units such as, but not limited to, ppm and/or $mg/m^3$. With the indicia provided on the extensions or scale wings, embodiments of the gas detector tube may comprise significantly more surface for incorporating information such as an increased number of scales, larger size scales, greater resolution of gas concentration readings, and additional information concerning the type of reagent, compensation factors, expiration date, as well as other information regarding use of the tube.

Indicia

Embodiments of the detectors may comprise indicia that may be read visually be the user of the gas detector tube and/or electronically or optically by a gas detector tube reader. For example, the gas detector tubes may comprise 2 to 4 different scales for visual reading of the gas concentration. The scales may include different sample volumes such as a scale for one stroke of the piston pump, a scale for five strokes of the piston pump wherein each volume has a scale in different units. The visually readable information may further include at least a portion of information selected from the group of information comprising the type of tube, range of exposure, recommended volume of sampling, expiration date, part and lot numbers and an indication of the direction of flow during sampling.

In addition to the scales, the gas detection tubes may further comprise electronically or optically readable information for the calibration of a data readable optic-electronic gas detector tube reader, for example. The optically readable information may be comprised in a bar code or other coded information of the information may be both typical visually and optically readable information. However, neither the electronically readable indicia nor the visually readable indicia should obstruct optically or visually reading the color of the reagent before sampling or the change of the reagent after sampling. In certain embodiments of the gas detector tubes, the indicia includes electronically readable information such as the type of tube, the target gases reactive with the reagent, the limits of the gas concentration range, a calibration curve, an expiration date, an unreacted or pristine color of the reagent, and allowable color change range, environmental correction factors of curves, an expected color change and color density/saturation of the reacted reagent.

In certain embodiments, the scale divisions may cover at least 80-95% of the total length of reagent and optically coded information is imprinted outside of this range so as to not interfere with visual reading of the gas concentration. The indicia may further comprise a color of the pristine reagent and a color of the reagent after contact with the target gases.

Gas Detector Tube Reader

Embodiments of the invention include a gas detector tube reader capable of reading the electronically and/or optically readable information on the detector tubes and the length of stain in a gas detector tube. Embodiments of the gas detector tube reader may comprise a holder for receiving a gas detector tube, an information reader capable of reading electronic or optically coded information from the gas detector tube, an optical reader capable of determining the length of stain in the gas detector tube, and a central processing unit. As used herein, a central processing unit (CPU) is a portion of a computer system that carries out the instructions of a computer program and performs the basic arithmetical, logical, and input/output operations of the system. The term central processing unit also includes both distributed processing systems and multiple central processing units. The CPU is in communication with a computer memory device capable of storing the optically or electronically read information from the gas detector tube. As used herein, computer memory refers to the physical devices used to store programs and/or data on a temporary or permanent basis for use in a computer or other digital electronic device. The computer memory storage device may be at least one of RAM, DRAM, SRAM, tape, magnetic disk, optical disks, flash memory, compact disk, DVD, and/or addressable semiconductor memory. A portion of the memory may be read only memory for storing information concerning the canister or gas mask that is more permanent such as, but not limited to, the canister identification, the chemical sorbent in the canister, the compounds capable of being absorbed or adsorbed on the chemical sorbent, the amount of chemical sorbent in the canister, the general capacity of the chemical sorbent, the capacity of the chemical sorbent for a specific target compound, the date of the manufacture of the canister, and/or the expiration date of the canister, for example. Other digital memory may be read/write memory. The term "memory" is often associated with addressable semiconductor memory, i.e. integrated circuits consisting of silicon-based transistors, used for example as primary memory but also other purposes in computers and other digital electronic devices.

The holder may be a complementary shape to receive the transparent tube of the gas detector tube. The holder may also have a locating system for accurately placing the gas detector tube in the electronic reader. The locating system has components that work in conjunction with components of the gas detector tube to allow for repeatably and accurately placing the gas detector tube in the holder of the gas detector tube reader and may be any components that are capable of aligning the gas detector tube in the reader as previously described.

Further embodiments of the optic-electronic gas detector tube reader are capable of compensating for any effects on reading as a result of relative humidity, temperature and barometric pressure. Such embodiments of the gas detector tube reader may comprise at least one environmental sensor selected from a temperature sensor, a pressure sensor, or a relative humidity sensor; wherein each sensor is in communication with the central processing unit. A central processing unit of the gas detector tube reader is capable of estimating a concentration of target gases in a sample from the length of stain and correcting the gas concentration using compensation factors specific to the gas detector tube and the output of the environmental sensors.

Determination of a more accurate estimation of an actual concentration using gas detector tube should incorporate compensation for environmental factors. An embodiment of the optic-electronic gas detector tube reader can read the calibration and compensation data from each gas detector tube. The calibration and compensation data, measured concentration and compensated concentration may be depicted on a display on the optic-electronic gas detector tube reader and/or communicated to another processing unit for display and recordation. The displayed or communicated data may include, but is not limited to, the type of tube in the reader, the target gases, measurable concentration range of the tube, tube accepted/rejected upon introduction of an internal standard and/or expiration date, concentration measured, ambient environmental conditions including, but not limited to, relative humidity, temperature, barometric pressure, total % of compensation applied to the measured gas concentration to determine a estimated concentration, as well as other desired information. In an embodiment of the gas detector tube reader, the optically or electronically coded information read from the gas detector may be displayed prior to sampling to verify the correct tube is being used, followed by the measured data for the ambient environmental conditions and tube acceptance.

Embodiment of the gas detector tube reader may comprise a sampling pump or may be a separate unit independent of the sampling pump. Embodiments of the gas detector tube reader comprise a holder for the gas detector tube having at least one illuminating source capable of providing illumination of the optically readable information and the reagent. Preferably, the illuminating source provides each of red, green, and blue colors with separately or in combination to produce white light. The gas detector tube reader will also comprise light sensors capable of read individual colors separately or mixed as white light. In certain embodiments, the gas detector tube reader may comprises means for inputting the altitude above sea level of the sampling location such as a keypad or dial adjustable by hand to different altitudes with increment 250 or 500 meters above sea level, for example, wherein each increment step corresponding to roughly 250 meters ~3% or to 500 meters ~6% of the scale of read concentration values.

In a specific embodiment, the gas detector tube reader comprises at least two light sensors and one illuminating light source on each side of a reading head. The reading head comprises two halves (shells) that are hinged together to from the holder to receive the gas detector tube. The shells comprising a locating system to accurately place the gas detector tube adjacent to the light sensors and light source. In certain embodiments, a first light sensor is situated very close to the inlet portion of the chemical reagent. This sensor may be used to read the color of the chemical reagent prior to sampling in an area close to the inlet plug. Before the sampling period the signal of this sensor is compared to the expected level of this signal as determined from the electronically or optically coded information on the gas detector tube. If the color of the reagent close to the inlet is outside an acceptable range, the gas detector tube reader will indicate that the tube should not be used. This ensures that the tube will still be able to accurately measure target gas concentrations. If a gas detector tube is improperly stored its shelf life may be reduced.

A second light sensor may be situated along the length of the color change reagent. The information signal from the second sensor is summarized with the signal of the first sensor and thus supplies information for the color intensity along the reagent layer. Practically the first sensor is very small lengthwise portion of the main sensor which is separated electronically and is able to read separately from the second main sensor or its signal could be added to the signal of the second sensor.

The colorimetric tubes can have linear dependence from the concentration—linear-colorimetric tube (length-of-stain) or the entire volume can change gradually to certain color more at the beginning and less at the end of the scale of the tube. In a regular case when the color after prescribed volumes falls within the readable scale, the reading system integrates the signal from first and second sensors and all lengthwise color change or all color change (color result as color intensity or density whichever is more dependent from the exposure) and compares these changes to a calibration curve data provided by the optical code.

The lines of the light sources and the sensors may be situated at approximately 45 degree angle from one another. For example, one line of sensors and two lines of light sources (each one capable to generate separate RGB color light) in each of the jaws. In bottom jaw 23, there is a movable pin-lock which clicks into a special opening or notch in scales wing 14a. As the opening 31 is placed on one only scale wing 14a there is no way for the tube to be put wrongly or misarranged.

Once the pump is activated and the air start flowing trough the tube the reagent layer 15 will start changing with the first portions of the substance of interest. Immediately after air with targeted substance start flowing in that reagent layer the sensors 56 and 57 will start integration of the signal and comparison to data already introduced by optical code calibration. In a typical sampling operation, only one stroke of the piston pump will be required to read the target gas concentration for the expected range of gas concentrations. During sampling, the output from the first sensor and the second sensor are integrated. The integrated signal from sensors 56 and 57 and signal from adjustable dial 51 (introducing correction for altitude) are transferred to Central Processing Unit (CPU) and processed to compensate optically read signal from the colorimetric tube and read such signal according to genuine calibration curve.

As the calibration of the tube is originally perform after production in controlled and steady ambient conditions, the gas concentration read from the tube should be corrected for differences in the temperature and relative humidity at the time of sampling. The environmental sensors for ambient temperature, relative humidity, and barometric pressure communicate with the central processing unit to be process the output according to calibration and validation data read from the gas detector tube reader.

The measured gas concentration may then be corrected based upon the barometric pressure or altitude, ambient air temperature and relative humidity. The corrected gas concentration of the target gases may be shown on Liquid Crystal Display (LCD) 80 as concentration units ppm or $mg/m^3$.

In situations when the concentration of the sample gas is low and no significant color change is measured or observed on the reagent after passing a typical volume of sample through the gas detector tube (one stroke of a piston type sampling pump, for example), the gas detector tube reader may detect an insignificant or no color change and indicate further greater sampling volume is required to properly read the target gas concentration. As the gas detector tube reader observes a significant and readable color change, the sampling may be stopped and the total sampling volume is integrated. In this way, a gas detector tube may be used for measuring low concentrations of the target gases. However, some types of gas detector tubes may not be used to measure concentrations below their prescribed ranges.

The gas detector tube may also determine the concentration of gases above the concentration rage of the gas detector tube. If the concentration rage is above the range of the gas detector tube for the type and quantity of the reagent, the reagent may all be involved in the colorimetric reaction prior to the end of the sampled volume. In such a case, the signal of the light sensors over time may be analyzed to estimate the gas concentration of the target gases. The integrated signal for 100% color change is processed along with the time when 100% color change is achieved. This data is compared to a calibration curve and following the curve of vacuum/time performance of the sampling pump to determine the sampled volume at the time of complete reaction, the central processing unit may calculate the uncompensated gas concentration. In such case, the total quantity of target gases is known (the capacity of the reagent) and the sample volume is estimated. Once the volume is estimated, the concentration may easily be determined. In other embodiments, the gas detector tube reader comprises a flow meter for direct determination of the sampled volume.

As such, the gas detector tube reader may expand the applicable range of many types of gas detector tubes by allowing reading of target gas concentrations outside of the range of the concentration span printed on the scales for visual reading.

Further embodiments of the gas detector tube reader may comprise a pumping pressure sensor between the sampling pump and the gas detector tube. The output of the pumping pressure sensor is in communication with the central processing unit and may be used to estimate the flow rate through the gas detector tube. The pumping pressure sensor may indicate a low or no sampling flow situation if after a time period, 10-30 seconds, for example, the pumping pressure sensor does not indicate a subsequent rise in pressure. A low or no flow situation may occur if the tips of the gas detector tube were not removed or the gas detector tube was improperly installed, for example. The pumping pressure sensor may also indicate the end of the sampling cycle when the pressure returns to the starting pressure prior to sampling and be used for leak checking in testing mode prior to sampling. The pumping pressure sensor may be fluidly connected between pump intake and the tube reading outlet of the reader. In such embodiments, the gas tube reader may comprise a sealing mechanism for the outlet of the gas detector tube. The sealing mechanism may be an o-ring, rubber socket or other attachment ensuring a tight seal and is forming cavity with very small dead volume connected fluidly to the pumping pressure sensor.

The gas detector tube reader holder is capable of securing tubes within the reader holder. The holder may further comprise an adjustment mechanism to allow tube adjustment and zeroing of the gas detector tubes against tube reading sensors and optical code reading device.

Embodiments of a method of determining a concentration of target gases, comprise placing a tube in an optic-electronic gas detector tube reader, electronically reading information from the gas detector tube. The method may further comprise performing a presampling test of the gas detector tube and reporting an acceptance or rejection of the tube. Additionally, the method may comprise drawing a known volume of gas sample through the gas detector tube and optically reading the length of stain. After sampling, if applicable, the readout of the optic-electronic gas detector tube reader may display information including, but not limited to, a measured gas concentration, the compensation factors to be applied to the measured gas concentration, each compensation factor determined from a measurement of the ambient conditions sensors including, but not limited to, temperature, relative humidity and barometric pressure or altitude, for example.

Example

Gas Detector Tubes and Gas Detector Tube Reader

Embodiments of the gas detector tubes 10 are shown on FIGS. 1A-E and FIG. 2. The gas detector tubes 10 comprise a sealed transparent tube 11, a chemical reagent 15 capable of a colorimetric reaction with a gaseous chemical compound within the sealed transparent tube 11, at least one elongated extension 14 extending from the tube 11, and at least one length of stain measurement scale on the extension 14.

The embodiments of FIGS. 1A to 1E depict various cross-sectional areas of the transparent tube 11 including circular in FIGS. 1-B and 1-C, and polygon in FIG. 1-D and FIG. 1-F. The surface of the tube 11 is clean and clear of markings in the area of the reagent 15 for visual or electronic reading of the length of stain. The gas detector tube 10 comprises a transparent tube 11 comprising at least one inert material such as glass, acrylic, polycarbonates, copolymers of polyethylene and polypropylene, polyesters, etc. The extensions 14 comprising scales resemble wings ("scale wings") 14 and 14a are situated longitudinally parallel to the main axis of the tube 11. The tube 11 may be read visually and electronically. Visual reading is possible by using one of the four possible scales with divisions printed on scale wings 14 and 14a. Scales can be printed on both (top and bottom) sides of each scale wing 14 and 14a. The divisions of the scales can be related to different units of measure and/or different sampling modes such as the number of sampling strokes of a sampling piston pump. On FIG. 1-A, two units of measure are shown printed on scale 14 in ppm and scale 14a in mg/m3 for one sampling stroke. On the back side of scale 14 and 14a same units may be used for 2, 3, 5, or 10 sampling strokes, for example. There are no lines on the surface of the tube 11 in the area of the reagent. The gas detector tubes may further comprise a transparent covering 16. Conventional gas detector tubes comprise a scale with lines directly on the tube over the reagent. Such conventional scales may interfere or can mislead visual reading or may impair the light illumination and reflected light for optic-electronic reading.

Embodiments of the gas detector tubes 10 may comprise an adhesive 18 to stabilize the gas detector tube 10 in storage and transport. One of scale wings 14 or 14a, for example, may be attached by adhesive 18 to a surface of tube holder 19. Another version of preferred embodiment of colorimetric tube 11 shown as cross-section 1-C on FIG. 1 has one wing-scale only.

Another embodiment of the gas detector tube is shown in FIGs depicting more details of the information printed on the wing-scales including number of strokes 17d, units of measure the concentration 17e, expiration date, and part identification number (PIN). Further, optically readable information 17 containing data for electronic reading and for electronic compensation of readings is printed on the scale wings 14 and 14a. The first divisions of scales 14 and 14a begin at a predetermined by calibration distance from the back end of plugging material 12. On wing-scale 14 there is a side notch, recess or small aperture 31 with round or oval shape (to match with a wire locking knot 30 or similar means when tube is inserted into reading head 20 of the gas detector tube, shown further on FIGS. 4 and 5). The recess, aperture or notch 31 allows precise positioning of the tube 11 in the jaws or shells of the holder of the gas detector tube reader. The light and optical sensors of the reading head shown further in perspective view on FIG. 3.

Figure 3:
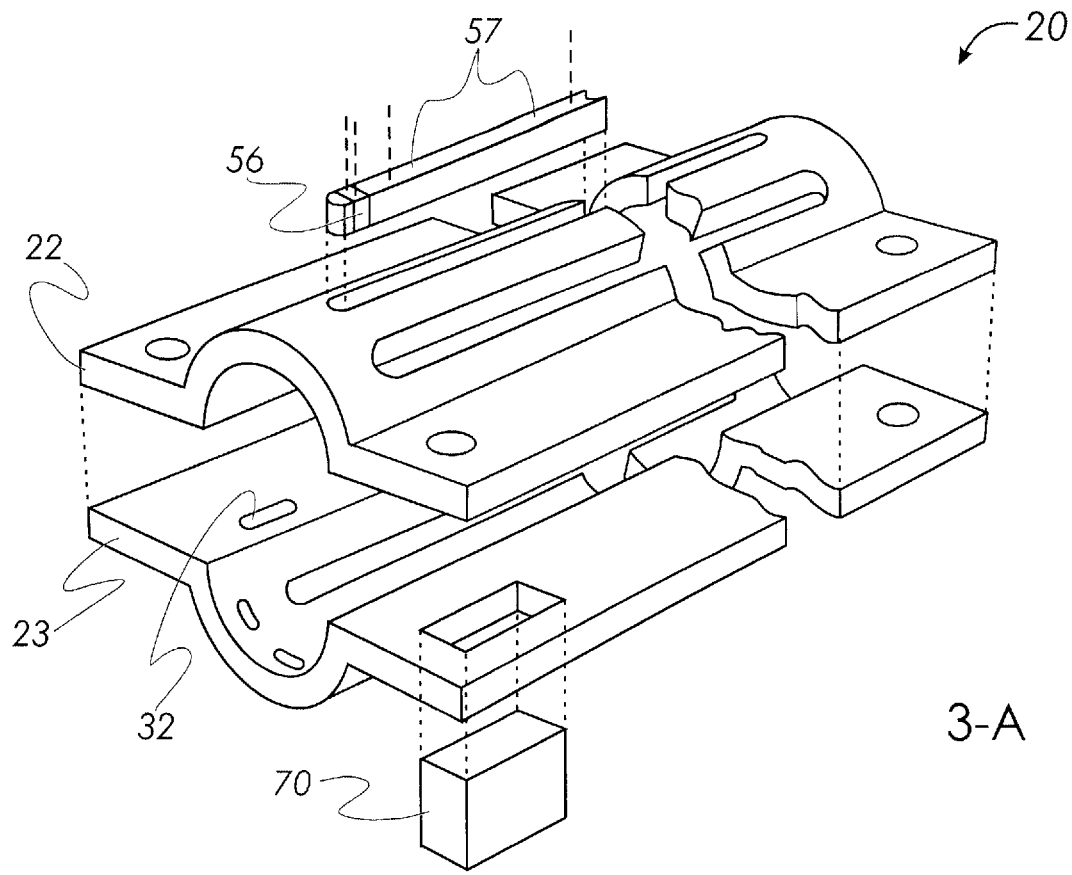
FIG. 3 depicts a reading head assembly of a gas detector tube reader.
Figure 3:
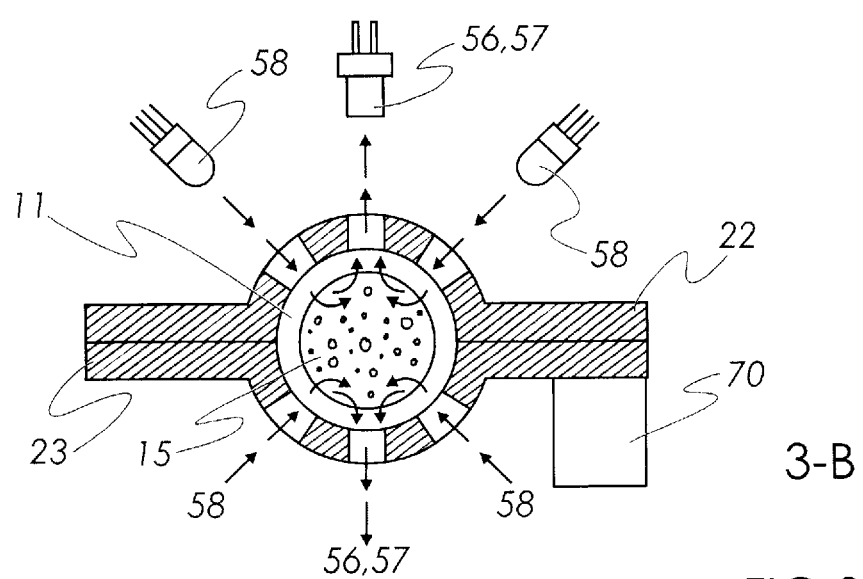

FIG. 3 depicts an embodiment of the reading head of the optic-electronic reader of the present invention. The reading head 20 comprises two main parts—upper jaw 22 and bottom jaw 23 which when closed are forming a cylindrical cavity or holder having a secure fit with gas detector tube 11, shown on the cross-section 3-B. On the bottom jaw, a locating system comprising an opening 32 in which a pin-lock 30 is capable of being moved up and down to thereby to click in the aperture 31 on the scale wing 14a when the tube is introduced into the cavity between top 22 and bottom 23 shells. The tube thus precisely placed for further illumination and reading.

In each jaw, two long illuminating sources 58 are positioned for illuminating the colorimetric gas detector tube inside of cylindrical cavity of the holder. As shown in FIG. 3-B, the cross-section of the reading head shows the position of the tube in the cavity. Both upper and bottom illuminating lines have axis angled approximately at 90 degree and approximately 45 degree to the main axis of the line of light sensors 56 and 57. Thus the light emitted from sources 58 illuminates the surface of the reagent layer 15 and penetrates deeper. The amount of reflected back light depends on the absorption and the dispersion of the light in the layer. Both of absorption and dispersion depend at least in part upon the color change of the reagent resulted from particular color reaction. The nature of color reading with linear light source and linear sensors suggest type of reading different from length-of-stain visual or electronic reading. As far as the linear sensor observes the color change over predetermined length as % of the total reflected light, for electronic calibration purposes a sharp front or leading edge of discoloration is not required. The reflected signal from the optical sensor will integrate color changes over the illuminated length regardless of whether color changes have sharp front or changes gradually in the total volume. At predetermined sampling volume the signal for reflected color-change and/or change of density is proportional to the sampled concentration. This is the base of main calibration mode—predetermined sampling volume. Embodiments of the gas detector tube reader are capable of determining the concentration of target gases based both on the length of stain and the color or color intensity of the reagent after exposure to target gases.

The signal generated by the sensors 56 and 57 may be proportional to the concentration of reflected light form the reagent. On the basis of this signal, the CPU would generate value of concentration comparing generated signal to the values from calibration curve. Those values are supplied to CPU by optical coded information 17 superimposed on one wing 14 and read by optical reading means 70 on FIG. 3. The optical code reading process my take place at the moment of inserting the tube through front slot of the reader head into cylindrical cavity formed between upper 22 and bottom 23 jaws. The view of the tube before insertion into the reading head is shown on FIG. 4. After insertion the tube is shown on FIG. 5. The inserted tube is secured by locking knot 30 and positioned into reading head. At the same time other compensatory signals are generated and transferred to CPU 50 to signal for altitude correction from dial 51, signals from temperature sensor 28 and from humidity sensor 24 shown on FIGS. 4, 5, 6. The sensors for temperature 28 and relative humidity 24 are placed in close proximity to the front part of the reading head and have access to ambient air. In this embodiment, the altitude above sea level for the sampling operation is input by the personnel performing the sampling process, therefore signal for altitude could be and is generated by hand driven potentiometer/dial 51. Small deviations of the local pressure due to weather factors are usually much smaller than 1% of the local barometric pressure and may be neglected.

Figure 5:
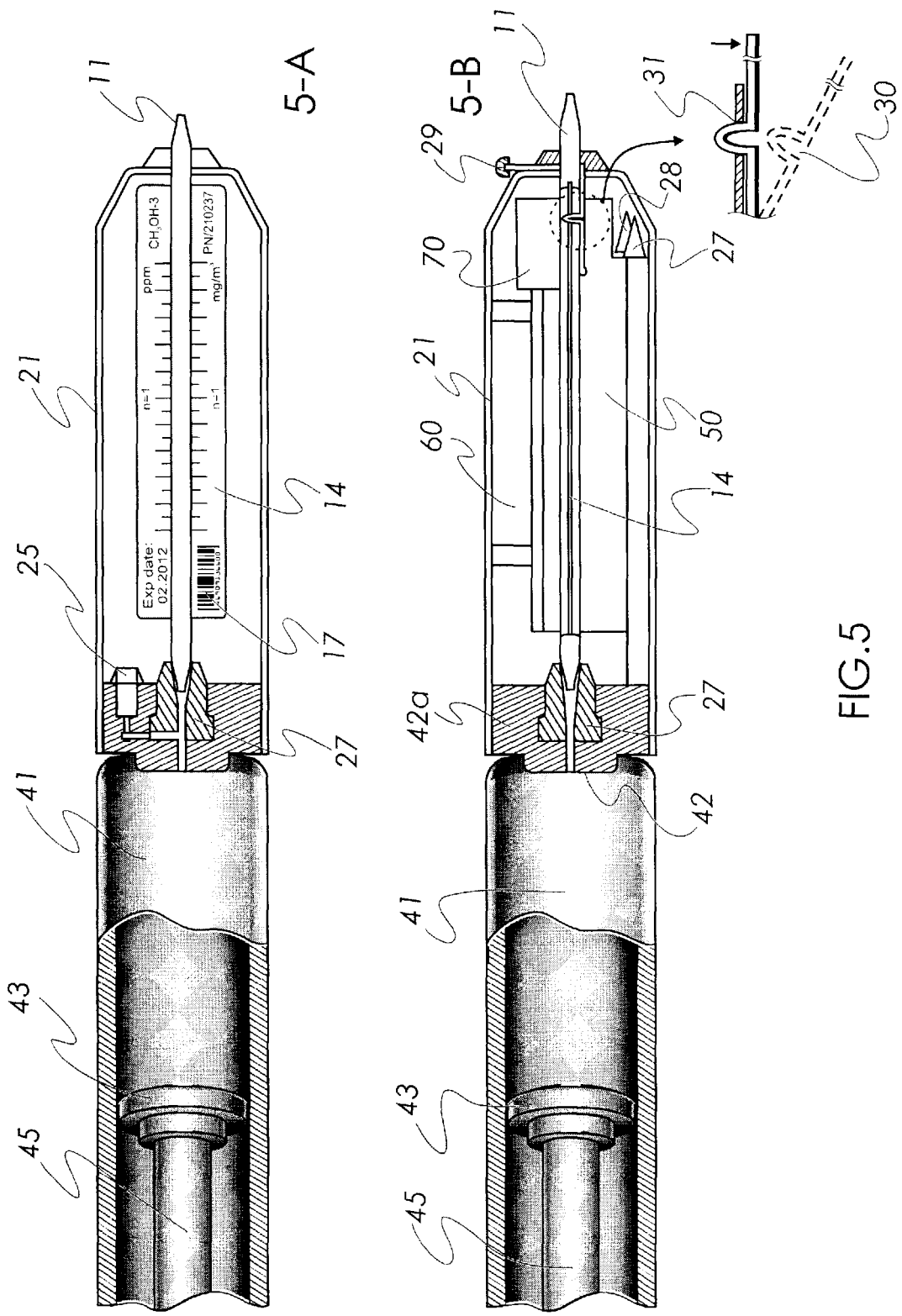
FIG. 5-A and 5-B are a cross-sections of the reading head assembled on the pump in two positions.

A sensor for pumping pressure 25 and pressure drop (from the environmental pressure sensor) on FIG. 5-A is fluidly connected to the space between a front rubber socket or other seal 27 of the pump and front of the pump piston 43 The pumping pressure sensor is electrically connected to CPU 50. The pumping pressure sensor 25 generates signal for vacuum and has two functions: to signal for predetermined pressure drop when piston is locked back for pump test and to determine whether socket 27 is filled by a tube 11 without broken tips 13, for example. In a pressure test if pressure signal doesn't change for a predetermined time, the CPU may indicate a good seal on the LCD-display 80 and send a sound signal that the pump and the system are considered reliable and sampling can be performed. The CPU can also send signal for malfunction if the pressure signal does not change during a sampling operation.

Another function of pumping pressure sensor 25 is to indicate the end of the sampling stroke and send signal for that to CPU. Sensor 25 may have additional function to send signal for sudden pressure drop (malfunction due to rupture or other causes) during the sampling period and the pumping pressure sensor may count the number of strokes of the pump and calculate a sample volume, for example.

Besides the described main sampling mode where tube is used within its normal concentrations span two other modes are possible:

If the concentration is significantly higher than the exposure concentration span calibrated for 1 stroke, the CPU will stop integrating the reflected signal at the point when this signal shows 100% color saturation. As the time of one (or more) stroke cycle is introduced by optical code, CPU estimates concentration on the base of sampled volume necessary for 100% color saturation (determined by calibration). LCD display will show concentration value along with a symbol (star) marking that the value is approximated.

If the concentration is very low and no signal for color change is generated during regular stroke cycle the CPU can urge for more strokes (2 to 10 if certain tube allows approximation of this type). The final concentration will be calculated by CPU on the base of larger sampled volume for achieving predetermined color results. The value of the concentration will be displayed with symbol showing that the value is approximated.

Signals from different sensors may be used for compensating for ambient conditions known to have influence on the value of the determined concentration. The factors obtained during the calibration and validation process of the tube and respective correction data along with data for hermeticity of the system are transferred to CPU for processing with the signals for other observable parameters such as the concentration and correction factors. By pressing communication buttons 82, 83 and 84 seen on FIG. 4 and FIG. 6 the values of measured temperature, relative humidity and calculated for certain temperature absolute moisture content can be obtained on display 80 as well as the value of entered by altitude compensation dial 51.

Figure 4:
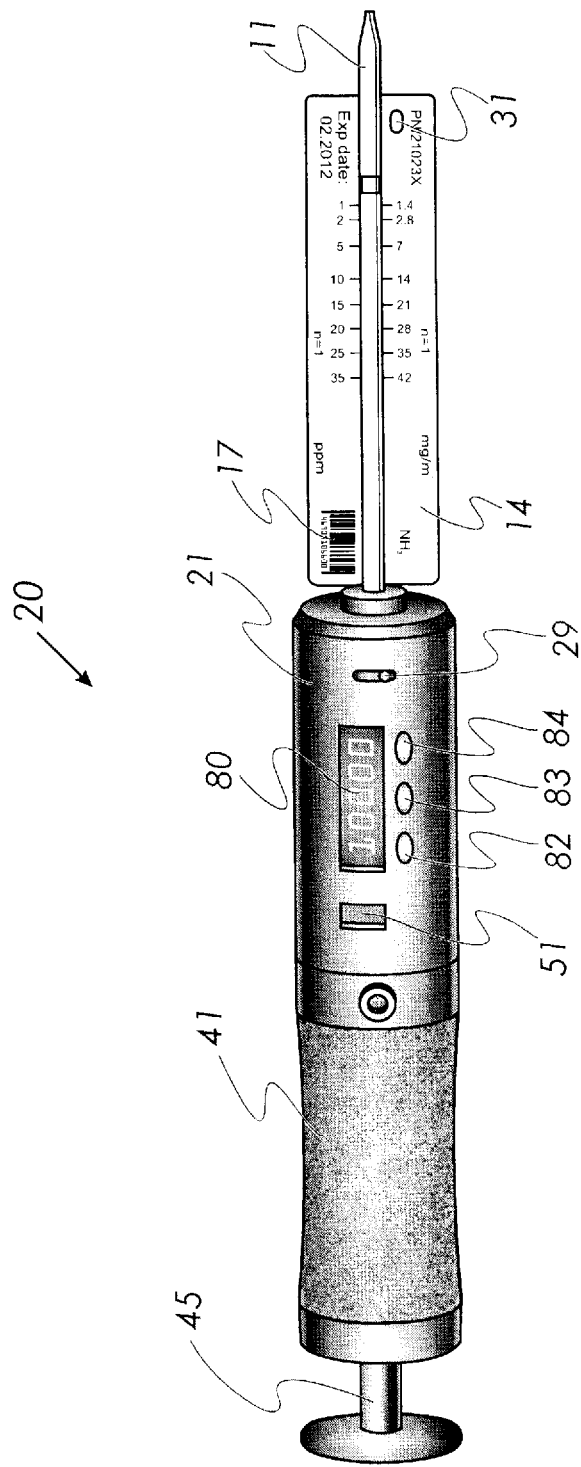
FIG. 4 is a perspective view of piston pump unit connected to a gas detector with tube reader and gas detector tube secured in the holder.

The aforementioned embodiment is connected and designed to be used with piston type hand pump shown as assembly on FIG. 4 and as side view cross-section on FIG. 5. The reading head 20 is enclosed into cylindrical enclosure 21 designed as extension of hand pump 41 and connected together by element 42*a* and socket 42. The wings 14 shown in front are separating top and bottom jaws (not seen in this position). The tube 11 with broken ends is positioned into rubber inlet 27 which is fluidly connected to the vacuumed space in pump 41 and with pressure drop sensor 25.

On the side view cross-section FIG. 5-B the tube 11 is shown precisely positioned into the cavity by locking pin 30. The optical code 17 is read by the optical code reading means 70. Also, shown is an energy supply 60, CPU 50 and at the front of the reader are sensors 24 and 28. By pushing down pin head 29, the locking pin 30 is going down and inserting the tube 11 is possible. At the beginning of this insertion optical reading means 70 are reading the optical code 17. Top and bottom jaws on both sides of scale wings are not shown here for simplicity.

Figure 6:
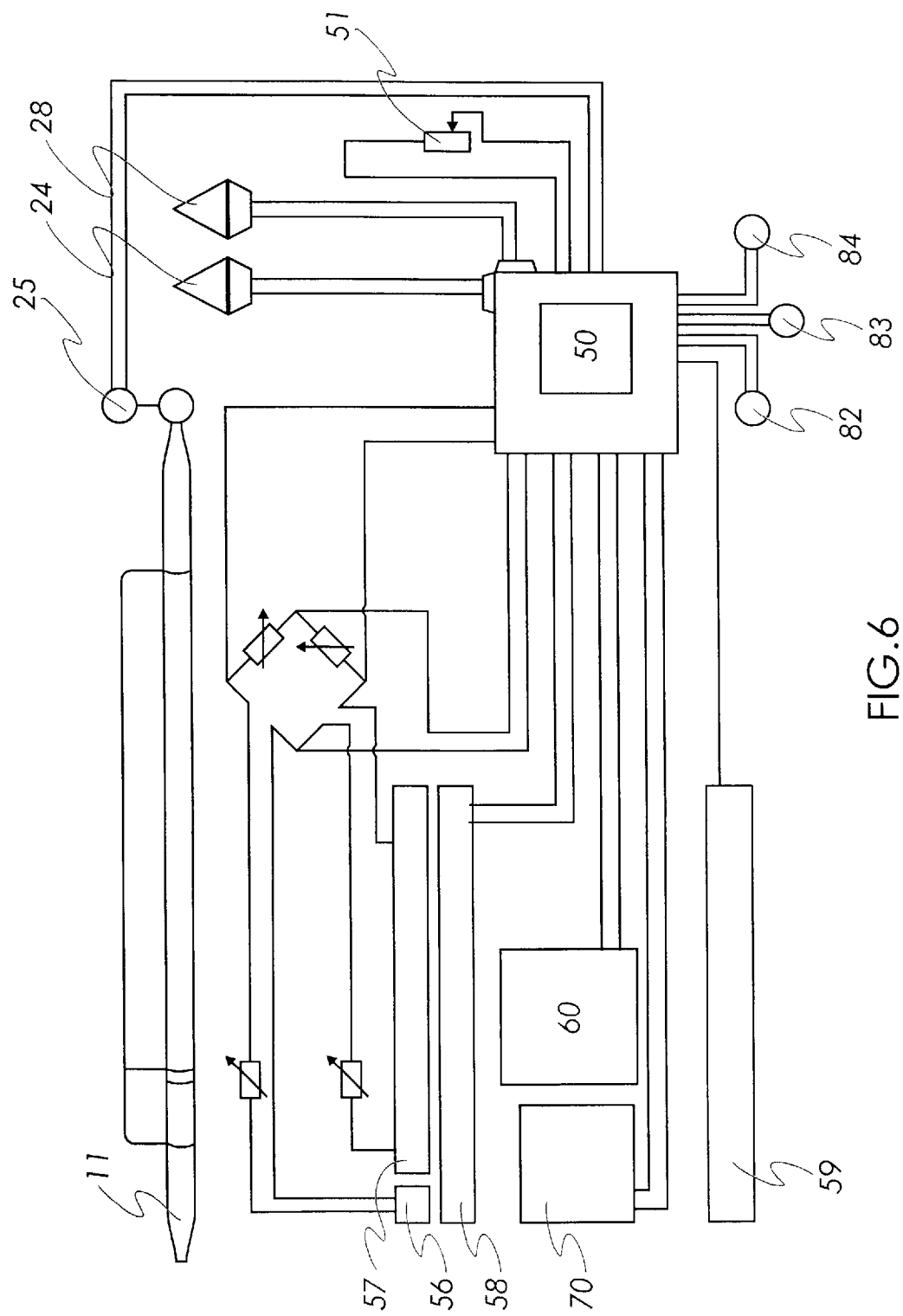
FIG. 6 is an electrical schematic diagram of optic-electronic reading unit reader depicting the electrical connections between the central processing unit the sensors and other components.

The process of reading and data integration of the reader assembled with piston type pump 41 and the main interconnections are shown as electronic schematic diagram on FIG. 6.

Figure 7:
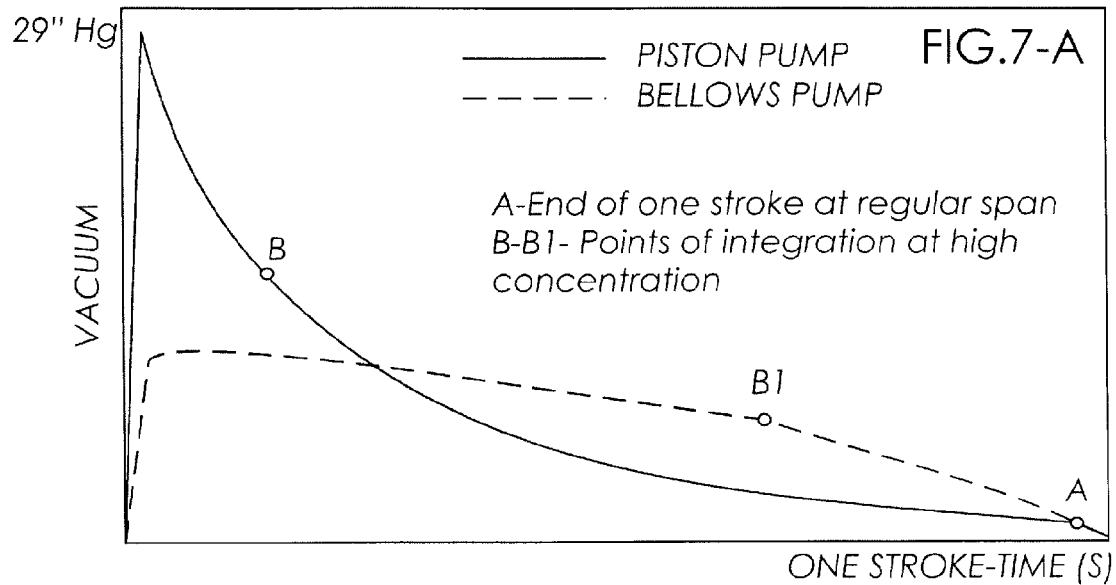
FIGS. 7-A and 7-B shows graphs representing point of stopping and integration for three basic working modes of the reading device integrated to piston type hand pump.
Figure 7:
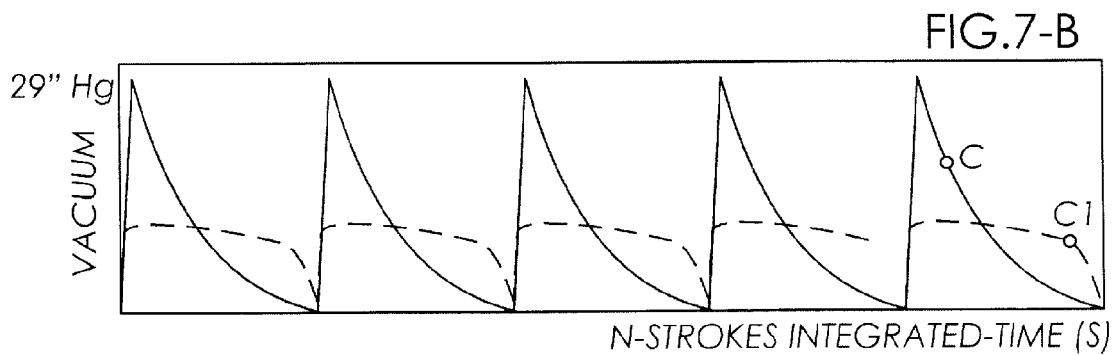
Figure 7:
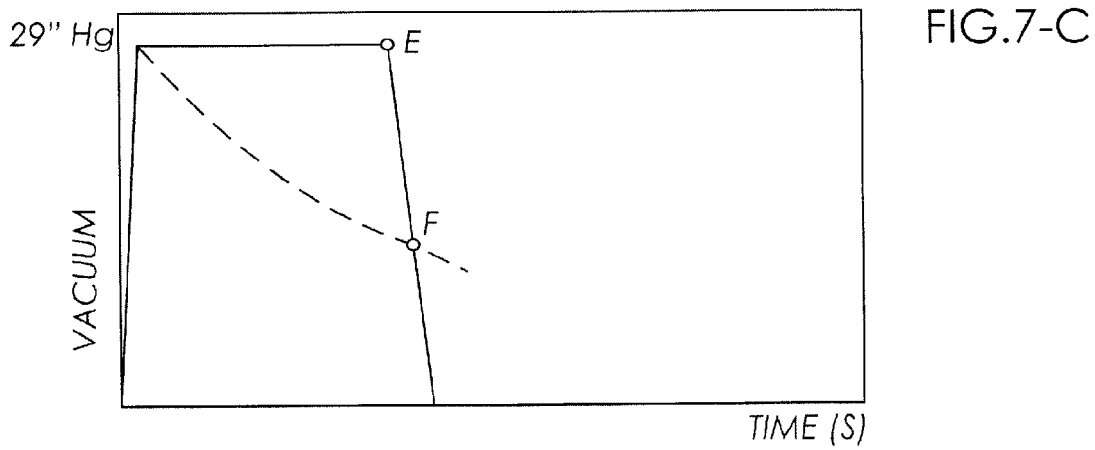

The process of pump-vacuum cycle(s), moment of reading and integration are shown on FIG. 7-A to C. When the sampling process is according to expected concentrations span the color change is read after the END of one or more predetermined count of strokes. The printed on the tube visual information as well as optical coded one will urge to appropriate stroke numbers (one stroke is considered most common case). The curves representing vacuum as a function of time laps FIG. 7-A for two basic styles of hand pumps (bellows and piston pumps) are different. This difference is a result of type of vacuum characterizing both pump styles. As seen on FIG. 7-A piston pump develops high vacuum at the very beginning and it gradually drops to atmospheric pressure for full time stroke. The bellows pump style develops lower and moderate vacuum lasting till the end of stroke. As the fluid velocity governed by the level of vacuum is different during the stroke, the calibration curves for both pump styles have some differences. The integrated area under the vacuum curves for both pumps represents the sampled volume and is usually the same—100 ml. per stroke. On this FIG. 7-A is depicted the process of reading very high concentrations exceeding tube calibration span for visual reading. There are shown two points—B/B1 representing respectively the positions when the color change rises to 100% and the process of integration of color change stops. The sampled volume could be different even with same type of tubes. This fact explains why at very high concentration the point B—unbroken line (for piston pump) has different time lap from point B1—dashed line (for bellows pump).

The CPU uses the time laps corresponding to points B/B1 to generate estimated concentration data, based on preliminary exposure data transferred by optical code 17.

At very low concentrations on FIG. 7-B the sampling volume of recommended one (or more strokes) may be not enough to generate color detectable from the first sensor 56 (FIG. 3). The sampling may be stopped or the reader can urge on the LCD-display for more strokes if this low concentration can be measured by??? certain type of tube by increasing the sampled volume (more sampling strokes). The process may take several strokes until first readable signal from sensor 56 is sufficient. The sampling stops at points C/C1 on FIG. 7-B.

If a proper calibration is done the reading may be successful. Not all types of tubes allow such calibration and approximation.

FIG. 7-C describes the process of vacuum check for piston pump. Vacuum is checked by sensor 25 (FIGS. 5 and 6). The vacuum should be stable for certain period of time illustrated by curve between points D and E. If the vacuum drops to any point below E such as point F the seal is not vacuum tight and sampling may not be accurate. The reader will give corresponding sound and light signal. If the vacuum detected by sensor 25 suddenly drops to zero during the sampling cycle the reader should abort sampling process and give audible and/or visual signal.

The calibration can be very successful at all type conditions. One and same type of tube can be used and read with different types pumps if the calibration conditions are introduced by optical code 17 for the used type of pump.

It is in the spirit of the present invention to use the same type of reading approach with any type of sampling pump used with colorimetric tubes such as bellows pump or piston pump. None of the main features or schematic diagrams needs to be changed except the way of connecting the pump to reader and way of calibration. As far as the bellows pump delivers much lower but more permanent vacuum which is the driving force in the sampling process—only calibration curve of the tube need to be changed.

The present invention suggests a system of two parts—tube and tube reader, each one having unique features and unique advantages. The design of the colorimetric tube allows the tube to be sampled and read visually or by suggested electronic reader which is impossible with all market available tubes. The design with wing-scales is advantageous permitting up to four scales for different sampling conditions and different units of measure. The design allows tubes to be much more safety in use and easy to transport and package. The design suggests also tubes with flat sides for easy reading avoiding reflection of cylindrical surface. The design assumes use of transparent plastics which is a big safety and manufacturing feature decreasing also manufacturing costs.

The design of tube reader advantageously suggests besides reading the color corresponding to certain exposure doses self introduction of the correction factors for temperature, humidity and altitude which will make final result much more reliable. The tube reader will allow reading of very low and very high concentrations beyond the calibration span printed on the scales.

The embodiments of the described gas detector tubes, gas detector tube readers and methods are not limited to the particular embodiments, components, method steps, and materials disclosed herein as such components, process steps, and materials may vary. Moreover, the terminology employed herein is used for the purpose of describing exemplary embodiments only and the terminology is not intended to be limiting since the scope of the various embodiments of the present invention will be limited only by the appended claims and equivalents thereof.

Therefore, while embodiments of the invention are described with reference to exemplary embodiments, those skilled in the art will understand that variations and modifications can be effected within the scope of the invention as defined in the appended claims. Accordingly, the scope of the various embodiments of the present invention should not be limited to the above discussed embodiments, and should only be defined by the following claims and all equivalents.

The invention claimed is:

1. A gas detector tube, comprising:
a sealed transparent tube;
a chemical reagent capable of a colorimetric reaction with a gaseous chemical compound within the sealed transparent tube;
at least one elongated extension fixedly attached to and extending from the tube along a longitudinal axis, wherein the at least one elongated extension comprises electronically or optically readable tube information describing characteristics the of chemical reagent in the gas detector tube; and
at least one visually readable length of stain measurement scale on the extension.

2. The gas detector tube of claim 1, comprising a transparent plastic adhered to a surface of the transparent tube and a surface of the elongated extension.

3. The gas detector tube of claim 1, wherein the transparent tube does not comprise a length of stain measurement scale.

4. The gas detector tube of claim 3, wherein there is no indicia printed or etched on surface of the transparent tube.

5. The gas detector tube of claim 1, wherein the chemical reagent comprises a porous solid with pathways that allow gas to flow through the porous solid.

6. The gas detector tube of claim 1, wherein the reagent is retained within the tube between two porous plugs.

7. The gas detector tube of claim 2, wherein the transparent plastic is adhered to the tube by at least one of physical means, shrink wrapping, or adhesive.

8. The gas detector tube of claim 7, wherein the adhesive is a permanent neutral transparent adhesive layer.

9. The gas detector tube of claim 2, wherein the transparent plastic is conformable to at least a portion of an exterior of the tube.

10. The gas detector tube of claim 1, wherein the extension is an elongated rectangular shape.

11. The gas detector tube of claim 1, wherein the extension comprises a pocket fixed along a main axis of the tube and capable of receiving a member comprising at least one length of stain scale.

12. The gas detector tube of claim 1, wherein the extension extends along a length of the tube at least as long as a distance between the two porous plugs.

13. The gas detector tube of claim 1, wherein the electronically or optically or readable information comprises at least one of a type of tube, target gases, limits of the gas concentration range of the chemical reagent, a calibration curve, expiration date, initial color of the chemical reagent, allowable color change after certain edging, chemical reagent color after contact with colorimetric reaction, color density/saturation of the reacted chemical reagent, or expected color change and color density/saturation of the unchanged chemical reagent.

14. The gas detector tube of claim 1, wherein the visually readable information includes at least one of type of tube, range of exposure, recommended volume of sampled gas, expiration date, part and lot numbers, or an indication of the direction of flow during sampling.

15. The gas detector tube of claim 1, wherein the gas detector tube comprises a second extension attached on an opposite side of the transparent tube as the extension.

16. The gas detector tube of claim 15, wherein the two extensions are substantially in the same plane.

17. The gas detector tube of claim 15, wherein the two extensions are in different but substantially parallel planes.

* * * * *